US011589906B2

(12) United States Patent
Almarza et al.

(10) Patent No.: US 11,589,906 B2

(45) Date of Patent: Feb. 28, 2023

(54) BIODEGRADABLE, MAGNESIUM-CONTAINING BONE SCREWS, METHODS FOR THEIR PREPARATION AND MEDICAL APPLICATIONS THEREFORE

(71) Applicant: UNIVERSITY OF PITTSBURGH—OF THE COMMONWEALTH SYSTEM OF HIGHER EDUCATION, Pittsburgh, PA (US)

(72) Inventors: Alejandro Jose Almarza, Pittsburgh, PA (US); John A. Holmes, Pittsburgh, PA (US); William Lee Chung, Mars, PA (US); Sarah E. Henderson, Irwin, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 127 days.

(21) Appl. No.: 17/065,199

(22) Filed: Oct. 7, 2020

(65) Prior Publication Data

US 2021/0030454 A1 Feb. 4, 2021

Related U.S. Application Data

(63) Continuation of application No. 14/185,007, filed on Feb. 20, 2014, now Pat. No. 10,849,667.

(Continued)

(51) Int. Cl.

*A61B 17/86* (2006.01)
*A61L 31/02* (2006.01)

(52) U.S. Cl.

CPC ........ *A61B 17/8605* (2013.01); *A61B 17/866* (2013.01); *A61L 31/022* (2013.01); *A61B 17/8635* (2013.01)

(58) Field of Classification Search

CPC .............. A61B 17/8605; A61B 17/866; A61B 17/8635; A61B 2560/04; A61B 2560/00;

(Continued)

(56) References Cited

U.S. PATENT DOCUMENTS 3,466,748 A 9/1969 Christensen
4,653,486 A 3/1987 Coker (Continued)

FOREIGN PATENT DOCUMENTS

EP 3995094 A1 * 5/2022 ......... A61B 17/8047

*Primary Examiner* — Paul B Prebilic

(74) *Attorney, Agent, or Firm* — Carol A. Marmo; Eckert Seamans Cherin & Mellott, LLC

(57) ABSTRACT

The invention relates to a biodegradable, magnesium-containing bone screw for implanting into a patient body for use in medical applications, such as, orthopedic, craniofacial and cardiovascular surgery. The bone screw has a head, shaft and tip. The thickness of the head is greater than the thickness of conventional bone screws. The shaft includes both a non-threaded and a threaded portion. The tip is non-threaded and pointed, such as, conical in shape. The composition of the bone screws provide for improved biodegradability and biocompatibility, and the features of the structure of the bone screws facilitate guidance and placement during implantation as well as reduce the potential for mechanical failures.

17 Claims, 1 Drawing Sheet

10
13
14
17
12a
16
18
15
12
20
TL
LP
12b
NL
L2
T
L1

Related U.S. Application Data

(60) Provisional application No. 61/767,812, filed on Feb. 22, 2013.

(58) Field of Classification Search
CPC .. A61L 31/00; A61L 2400/08; A61L 2400/18; A61L 2430/02; A61L 2430/38
See application file for complete search history.

(56) References Cited

U.S. PATENT DOCUMENTS

| | | | | |
|---|---|---|---|---|
| 5,578,034 | A | 11/1996 | Estes | |
| 5,693,055 | A | 12/1997 | Zahiri et al. | |
| 5,868,749 | A | 2/1999 | Reed | |
| 5,941,911 | A | 8/1999 | Buechel | |
| 6,162,225 | A | 12/2000 | Gertzman et al. | |
| 6,533,790 | B1 | 3/2003 | Liu | |
| 6,585,740 | B2 | 7/2003 | Schlapfer et al. | |
| 9,510,932 | B2 * | 12/2016 | Kumta | A61K 31/7036 |
| 9,539,068 | B2 | 1/2017 | Spagnoli et al. | |
| 2002/0004060 | A1 | 1/2002 | Heublein et al. | |
| 2005/0059972 | A1 | 3/2005 | Biscup | |
| 2005/0090826 | A1 | 4/2005 | Keller | |
| 2010/0145460 | A1 | 6/2010 | McDonough et al. | |
| 2011/0020768 | A1 | 1/2011 | Spagnoli et al. | |
| 2011/0060373 | A1 | 3/2011 | Russell et al. | |
| 2011/0172798 | A1 | 7/2011 | Staiger et al. | |
| 2012/0143227 | A1 * | 6/2012 | Steckel | A61L 31/148 606/151 |
| 2012/0310284 | A1 | 12/2012 | Gerchow | |

* cited by examiner

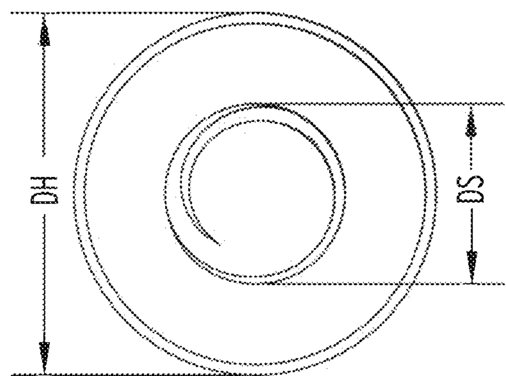
FIG.1C
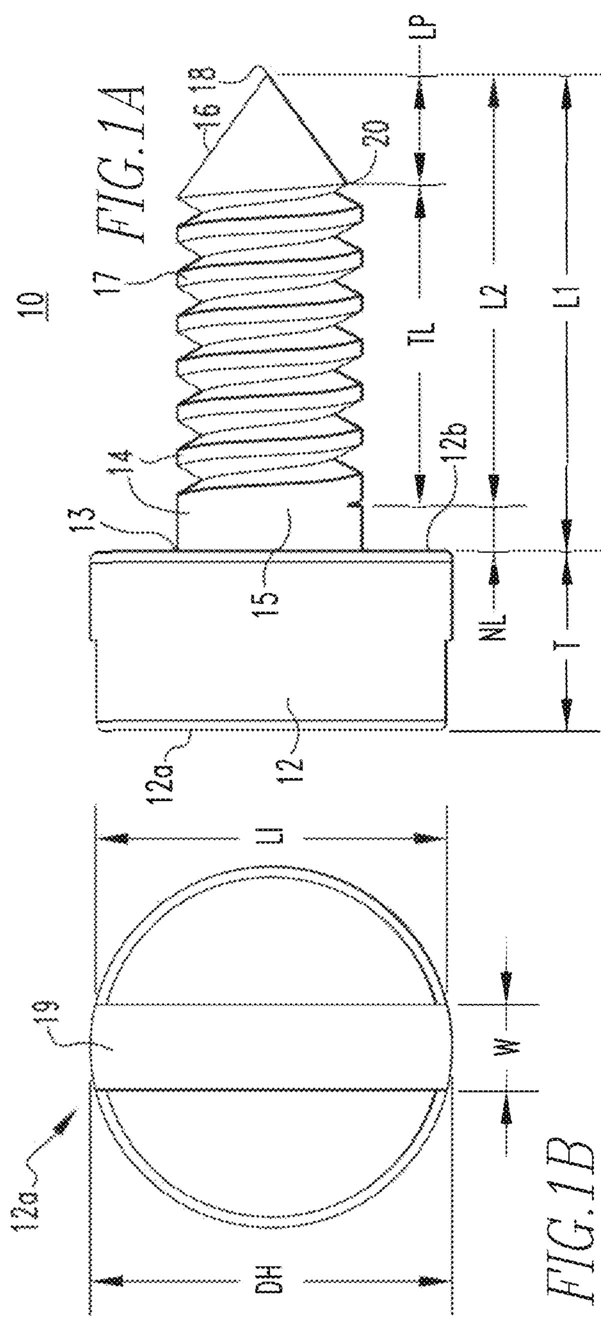
FIG.1A
FIG.1B
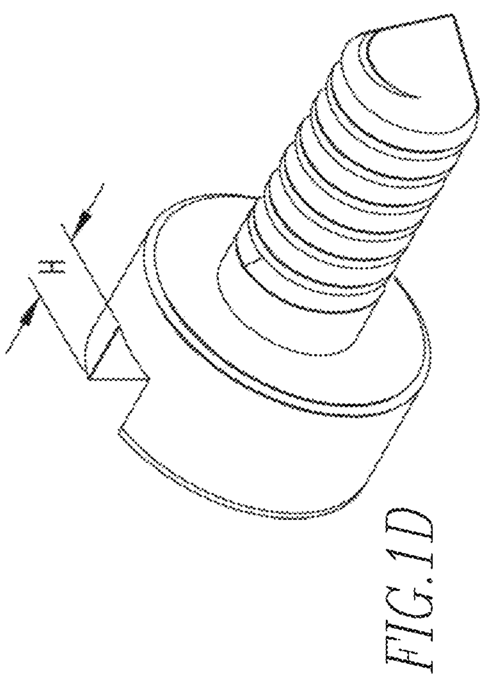
FIG.1D

BIODEGRADABLE, MAGNESIUM-CONTAINING BONE SCREWS, METHODS FOR THEIR PREPARATION AND MEDICAL APPLICATIONS THEREFORE

CROSS REFERENCE TO RELATED PATENT APPLICATIONS

This continuation patent application claims the benefit of priority under 35 U.S.C. § 120 from U.S. patent application Ser. No. 14/185,007 filed Feb. 20, 2014, entitled "Biodegradable, Magnesium-Containing Bone Screws, Methods for Their Preparation and Medical Applications Therefor," now U.S. Pat. No. 10,849,667, which claims the benefit of priority under 35 U.S.C. § 119(e) from U.S. Provisional Patent Application No. 61/767,812 entitled "Biodegradable, Magnesium-Containing Bone Screws, Methods for Their Preparation and Medical Applications Therefor", filed on Feb. 22, 2013, the contents of which are incorporated herein by reference.

GOVERNMENT SUPPORT AND FUNDING

The invention was made with government support under #0812348 awarded by the National Science Foundation. The government has certain rights in the invention.

FIELD OF THE INVENTION

The invention relates to biodegradable bone screws composed of magnesium-containing material, e.g., magnesium alloy, which are suitable as implant devices into a patient body for medical applications, such as, orthopedic, craniofacial and cardiovascular surgery.

BACKGROUND OF THE INVENTION

Metallic implant devices, such as plates, screws, nails and pins, constructed of stainless steel, cobalt-chromium and titanium alloys are commonly used in the practice of orthopedic, craniofacial and cardiovascular implant surgery. These materials exhibit good biomechanical properties, but are not degradable over a period of time. Thus, when the implant device is no longer needed, surgery is required for its removal. To reduce the need for surgery and risks associated therewith, it is a desire in the art to design and develop new biomaterials that are capable of degrading, e.g., dissolving, over time such that surgical removal is precluded. For example, polymers, such as polyhydroxy acids, polylactic acid (PLA), polyglycolic acid (PGA), and the like, are useful for the construction of implant devices. These materials, however, have been found to exhibit relatively poor strength and ductility, and have a tendency to react with human tissue resulting in limited bone growth. As a result, magnesium alloys have emerged as a new class of biodegradable materials for orthopedic applications. These materials exhibit properties comparable to natural bone, are non-toxic and capable of degrading, e.g., corroding, over time in a physiological environment, e.g., a patient body. In particular, magnesium degrades to produce a soluble, non-toxic corrosion hydroxide product which is harmlessly excreted through urine. To date, magnesium alloys have demonstrated the ability to regenerate both hard and soft musculoskeletal tissues, which is particularly valuable for engineering craniofacial degradable implants.

There are, however, disadvantages associated with bone screws composed of magnesium-containing material, e.g., magnesium alloy. For example, magnesium is generally a softer material than metal materials, e.g., stainless steel or titanium, conventionally used for implant devices. As a result, magnesium alloy bone screws have been found to be more prone to breakage. In certain instances, during the process of implantation, the heads of the magnesium alloy screws have sheared off, and the screws have been shown to be difficult to place in existing bone, e.g., difficult to align with a corresponding opening which is drilled into existing tissue in a patient to receive the screw.

Thus, there is a need in the art to design and develop a bone screw having suitable corrosion resistance, biodegradability and biocompatibility, while having an improved design structure so as to facilitate alignment and placement of the screw, and to demonstrate minimal breakage, e.g., of the screw head, during implantation.

BRIEF DESCRIPTION OF THE DRAWINGS

A further understanding of the invention can be gained from the following description of the preferred embodiments when read in conjunction with the accompanying drawings in which:

FIG. 1A is a side view of a bone screw in accordance with certain embodiments of the invention;

FIG. 1B is a top view of the bone screw of FIG. 1A in accordance with certain embodiments of the invention;

FIG. 1C is a bottom view of the bone screw of FIG. 1A in accordance with certain embodiments of the invention; and FIG. 1D is a perspective view of the bone screw of FIG. 1A in accordance with certain embodiments of the invention.

SUMMARY OF THE INVENTION

In an aspect of the invention, a biodegradable, magnesium-containing bone screw, is provided. The bone screw includes a head having a top surface, a bottom surface and a thickness extending between the top and bottom surfaces; a shaft having a first end and a second end and a length linearly extending between the first and second ends; and a non-threaded, pointed tip extending from the second end of the shaft. The first end of the shaft is coupled to the bottom surface of the head. A portion of the length of the shaft extending from the first end to a transition point is non-threaded and a remaining portion of the length of the shaft extending from the transition point to the second end of the shaft is threaded. The thickness of the head is greater than a conventional bone screw head thickness.

The top surface of the head can include an indentation diametrically formed therein. The indentation may have a length and height that is suitable to accommodate a driver mechanism for guiding and rotating the bone screw. The length of the indentation can extend along an entire diameter or nearly the entire diameter of the head.

In certain embodiments, the non-threaded portion of the length of the shaft is less than the threaded portion of the length of the shaft. Further, the tip may be cone-shaped.

The bone screw may be composed of magnesium alloy.

The bone screw may be employed as an implant device for medical applications. In certain embodiments, the bone screw is employed in craniofacial surgery.

In another aspect of the invention, a method of preparing a biodegradable, magnesium-containing bone screw is provided. The method includes preparing a magnesium-containing composition, melting the magnesium-containing composition at an elevated temperature, introducing the melted magnesium-containing composition into a mold, cooling and solidifying the mold. The mold includes a head having a top surface, a bottom surface and a thickness extending between the top and bottom surfaces, the thickness of the head being greater than a conventional bone screw head thickness; a shaft having a first end and a second end and a length linearly extending between the first and second ends, the first end of the shaft coupled to the bottom surface of the head, a portion of the length of the shaft extending from the first end to a transition point being non-threaded and a remaining portion of the length of the shaft extending from the transition point to the second end of the shaft being threaded; and a non-threaded, pointed tip extending from the second end of the shaft.

In still another aspect of the invention, a method of employing a biodegradable screw as a medical device to regenerate new tissue in a patient is provided. The method includes preparing a magnesium-containing bone screw in accordance with the above-described method, forming an opening in existing tissue in the patient, and implanting the bone screw into the opening in the existing tissue of the patient.

The existing tissue may be selected from craniofacial bone, orthopedic bone and cardiovascular tissue.

DETAILED DESCRIPTION OF THE PREFERRED EMBODIMENTS

The invention relates to novel, biodegradable bone screws constructed from magnesium-containing material, e.g., magnesium alloy, having an improved structure which is designed to facilitate alignment and placement, and reduce breakage of the bone screw, e.g., the head of the bone screw, during implantation. These bone screws are suitable for implanting into a body of a patient for medical applications, such as but not limited to, orthopedic, craniofacial and cardiovascular surgery.

A wide variety of magnesium-containing materials, e.g., magnesium alloys, may be employed to construct the biodegradable bone screws of the invention. Non-limiting examples of suitable materials include those described in PCT Application having International Application No. PCT/US2012/058939 entitled "Biodegradable Metal Alloys" filed on Oct. 5, 2012 and based on U.S. Provisional Patent Application 61/544,127 entitled "Biodegradable Metal Alloys" filed on Oct. 6, 2011; and U.S. Provisional Patent Application 61/710,338 entitled "Biodegradable Iron-Containing Compositions, Methods of Preparing and Applications Therefor" filed on Oct. 5, 2012, which are incorporated in their entirety herein by reference.

In certain embodiments, the bone screws of the invention are constructed of a composition including magnesium and one or more of iron, zirconium, manganese, calcium, yttrium and zinc. For example, suitable compositions include a combination, e.g., mixture or blend, of magnesium, iron, manganese and calcium, or a combination, e.g., mixture or blend, of magnesium, iron, zirconium and calcium, or a combination, e.g., mixture or blend, of magnesium, iron zinc and calcium. The amount of each of the components in the combinations/compositions can vary and in general, the amounts are selected such that the resulting combinations/compositions are within acceptable non-toxic limits, sufficiently biocompatible and degradable over a period of time. For example, the components and their amounts may be selected such that the combinations/compositions exhibit corrosion resistance in the presence of water and body fluids which allow for suitable in-vitro use in a physiological environment, e.g., patient body, and exhibit corrosion resistance with minimal or no evolution of hydrogen gas as the evolution of hydrogen, e.g., hydrogen bubbles, may cause complications in a patient body.

In certain embodiments, the composition for use in the invention includes from about 0.5 to about 4.0 weight percent of yttrium, from greater than zero to about 1.0 weight percent of calcium, from about 0.25 to about 1.0 weight percent of zirconium, and the remainder or balance being magnesium based on total weight of the composition. In other embodiments, the composition includes from about 1.0 to about 6.0 weight percent of zinc, from greater than zero to about 1.0 weight percent of zirconium, and the remainder or balance being magnesium based on total weight of the composition.

It is contemplated that other components may be added to the compositions provided that the non-toxicity, biocompatibility and degradability remain within acceptable limits. Acceptable non-toxic limits and time frames for degradation can vary and can depend on the particular physical and physiological characteristics of the patient, in-vitro site of implantation and medical use of the device. Non-limiting examples of suitable other components include aluminum, silver, cerium and/or strontium. In certain embodiments, each of the aluminum, silver, cerium and strontium may be present in an amount from about 1.0 to about 9.0 weight percent, from about 0.25 to about 1.0 weight percent, from about 0.1 to about 1.0 weight percent and from about 1.0 to about 4.0 weight percent, respectively, based on total weight of the composition.

In certain embodiments, the composition includes from about 0.5 to about 4.0 weight percent of yttrium, from greater than zero to about 1.0 weight percent of calcium, from about 0.25 to about 1.0 weight percent of silver, from about 0.25 to about 1.0 weight percent of zirconium, and the remainder or balance being magnesium, based on total weight of the composition.

In other embodiments, the composition includes from about 0.5 to about 4.0 weight percent of yttrium, from greater than zero to about 1.0 weight percent of calcium, from about 0.1 to about 1.0 weight percent of cerium, from about 0.25 to about 1.0 weight percent of zirconium, and the remainder or balance being magnesium, based on total weight of the composition.

In other embodiments, the composition includes from about 0.5 to about 4.0 weight percent of yttrium, from greater than zero to about 1.0 weight percent of calcium, from about 0.25 to about 1.0 weight percent of silver, from about 0.1 to about 1.0 weight percent of cerium, from about 0.25 to about 1.0 weight percent of zirconium, and the remainder or balance being magnesium, based on total weight of the composition.

In yet other embodiments, the composition includes from about 1.0 to about 6.0 weight percent of zinc, from about 0.25 to about 1 weight percent of silver, from greater than zero to about 1.0 weight percent of zirconium, and the remainder or balance being magnesium, based on total weight of the composition.

In still other embodiments, the composition includes from about 1.0 to about 6.0 weight percent of zinc, from about 0.1 to about 1 weight percent of cerium, from greater than zero to about 1.0 weight percent of zirconium, and the remainder or balance being magnesium, based on total weight of the composition.

In still other embodiments, the composition includes from about 1.0 to about 6.0 weight percent zinc, from about 0.25 to about 1 weight percent of silver, from about 0.1 to about 1 weight percent of cerium, from greater than zero to about 1.0 weight percent of zirconium, and the remainder or balance being magnesium, based on total weight of the composition.

Suitable compositions for use in the invention may be prepared using various methods and processes. The components, e.g., magnesium and one or more of iron, manganese, calcium, zirconium and zinc, may be melted or alloyed at an elevated temperature using conventional methods known in the art. In certain embodiments, the components are alloyed using high energy mechanical alloying (HEMA), uniaxial or isostatic compaction, and sintering. HEMA may be conducted under a protective atmosphere, e.g., in the presence of argon, sulfur hexafluoride and mixtures thereof, to preclude, minimize or reduce decomposition of the components in the composition. Subsequent to HEMA, amorphous films may be synthesized by pulsed laser deposition (PLD).

Further, it is known to use general casting methods and, forming and finishing processes, such as, extrusion, forging, polishing (by mechanical and/or chemical means), surface treating (to form a superficial layer), and combinations thereof, to produce the bone screws of the invention for use as implant devices. For example, a molten alloyed composition may be poured into a mold, allowed to cool and thereby solidify.

Suitable design structures for the bone screws can vary. In accordance with the invention, the bone screws have a head, a shaft and a tip. The head has a top surface, a bottom surface and a thickness extending between the top and bottom surfaces. The shape of the head, shaft and tip can vary. Typically, the head and shaft are cylindrical in shape such that the top and bottom surfaces of the head are circular. Further, as is typical with conventional screws, the diameter of the head is greater than the diameter of the shaft. The thickness of the head is greater than the thickness of a conventional bone screw head. The top surface of the head has an indentation diametrically formed therein. The indentation has a length and height that is suitable to accommodate a driver mechanism for rotating and guiding the bone screw. In certain embodiments, the length of the indentation extends along the entire or nearly the entire diameter of the top surface of the head. The shaft has a first end and a second end and a length linearly extending between the first and second ends. The first end of the shaft is coupled to the bottom surface of the head. A first portion of the length of the shaft extends from the first end to a transition point. This first portion is non-threaded. A remaining portion, e.g., second portion, of the length of the shaft extends from the transition point to the second end of the shaft. This second portion is threaded. In certain embodiments, the non-threaded portion extends over a shorter length of the shaft as compared to the length of the threaded portion. The tip is non-threaded, extends from the second end of the shaft and has a pointed end. In certain embodiments, the tip is cone shaped.

FIG. 1A shows a side view of a bone screw 10 structure in accordance with certain embodiments of the invention. In FIG. 1A, the bone screw 10 includes a head 12, a shaft 14 and a tip 16. The head has a top surface 12*a* and a bottom surface 12*b*. The shaft 14 has a first end 13 and a second end 20. The head 12 is positioned at the first end 13 of the shaft 14 and the tip 16 is positioned at the second end 20 of the shaft. As shown, the top and bottom surfaces 12*a* and 12*b* of the head 12 have a circular shape. However, it is contemplated that the head surfaces 12*a* and 12*b* can include various shapes. Further, as shown in FIG. 1B, the top surface 12*a* of the head 12 can have a diametrically positioned indentation 19 formed therein to accommodate a driver mechanism, such as a screw driver, (not shown) for rotating and guiding the bone screw 10. The shaft 14 includes a non-threaded region 15 and a threaded region 17. The non-threaded region 15 is adjacent to the head 12 and the threaded region 17 is adjacent the tip 16. The non-threaded region 15 extends from the first end 13 of the shaft 14 to the starting point of the threaded region 17 and the threaded region 17 extends from the ending point of the non-threaded region 15 to the second end 20 of the shaft. The tip 16 is non-threaded, conical in shape and has a point 18 on its end. It is contemplated that the point 18 facilitates insertion of the bone screw 10 into a patient's bone tissue (not shown).

The bone screws of the invention have a wider/taller or thicker head than conventional bone screws known in the art. As shown in FIG. 1A, the head 12 has a thickness T and as shown in FIG. 1B, a diameter DH. In certain embodiments, the thickness T can be from about 0.96 mm to about 1.04 mm or about 1.0 mm and the diameter DH can be from about 1.92 mm to about 2.08 mm or about 2.0 mm. Further, as shown in FIG. 1A, the shaft 14 and tip 16 have a combined length L1. In certain embodiments, the length L1 can be from about 2.58 mm to about 2.80 mm or about 2.69 mm. Also, as shown in FIG. 1A, a length L2 represents the combined length of the threaded region 17 and the tip 16. In certain embodiments, the length L2 can be from about 2.32 mm to about 2.52 mm or about 2.42 mm. As for diameter DS of the shaft 14, as is generally indicative of screws, the diameter DS is less than the diameter DH of the head 12 (as shown in FIG. 1C). In certain embodiments, the diameter DS can be from about 0.96 mm to about 1.04 mm or about 1.0 mm. Furthermore, as shown in FIG. 1B, the length of the indentation 19 is LI and its width is W. In certain embodiments, the width W can be from about 0.48 to about 0.52 mm or about 0.50 mm. In certain embodiments, the length LI can be equal to the diameter DH or nearly equal to DH. The height H of the indentation 19 is shown in FIG. 1D. In certain embodiments, the height H can be from about 0.48 mm to about 0.52 mm or about 0.50 mm. In certain embodiments, the length of the non-threaded portion NL can be from about 0.26 mm to about 0.28 mm or about 0.27 mm. In certain embodiments, the length of the threaded portion TL can be from about 1.84 mm to about 2.00 mm or about 1.92 mm. In certain embodiments, the length of the tip LP, as shown in FIG. 1A, can be from about 0.48 mm to 0.52 mm or about 0.5 mm.

Without intending to be bound by any particular theory, it is believed that the biodegradable bone screws according to the invention have one or more of the following advantages as compared to conventional bone screws known in the art:

(i) The use of a biodegradable magnesium-containing material or magnesium alloy material eliminates the need for surgery to remove the screws from the patient;

(ii) The enlarged head size and an adjacent non-threaded region of the shaft allows the screw to withstand the needed torque applied to the head of the screw during implantation into a bone; and (iii) The non-threaded tip disposed at the distal portion of the shaft allows for better guidance into the bone of the patient.

In certain embodiments, the bone screws of the invention are implanted into a patient body by forming one or more openings in existing tissue and inserting or implanting the bone screws within the opening(s). In certain embodiments, the bone screws are effective to regenerate tissue.

EXAMPLES

Bone screws were fabricated from commercially available pure Mg and a Mg aluminum zinc alloy (AZ31) purchased from Goodfellow (Oakdale, Pa.). The pure Mg was 99.9% pure, and the AZ31 alloy contained 2.5-3.5 wt % aluminum, 0.6-1.4 wt % zinc, and 0.2-1.0 wt % manganese with the remainder being Mg. Similarly sized, commercially available stainless steel screws were purchased from Small Parts (Seattle, Wash.) for comparison.

For in-vitro analysis, a mechanical test was designed to compare the holding strength of the pure Mg and AZ31 screws to stainless steel screws. A material testing system was set up for complete axial pull-out tests (MTS Insight, MTS Systems, Eden Prairie, Minn.). Synthetic bone made of solid rigid polyurethane foam (ASTM F-1839-08) from Sawbones (a division of Pacific Research Laboratories, Inc. Vashon, Wash.) was used as the control material for the pull-out tests. Screws were placed in the foam after the holes were predrilled and tapped. A testing rate of 5 mm/min was used according to ASTM standard F543-07. The maximum force needed to release the screw from the foam was recorded for each screw. Pure Mg and AZ31 screws exhibited pull-out forces similar to that for the stainless steel screws when pulled out of a synthetic bone material. The pull-out strength for all of these screw materials was approximately 40 N with no statistically significant differences between the groups.

For in-vivo analysis, the pure Mg and AZ31 screws were implanted in at least three different rabbits' mandibles for each time point of 4, 8, and 12 weeks. The screws were implanted in the mandible near the incisure of facial vessels, located where the curve of the mandible and the posterior end of the molar region meet. Two screws of the same material were placed in predrilled holes on one side of the mandible. Two screws of another material were placed on the opposite side of the mandible using the same procedure. Screw types were not mixed on a per side basis to avoid galvanic corrosion. The control rabbits were implanted and incubated for 12 weeks. The control groups included a group with stainless steel screws implanted, and a group where osteomies (holes) were drilled into the mandible but no screws were placed. Naïve control bone was also examined. MicroCT (computed tomography) was used to assess bone remodeling and Mg-alloy degradation, both visually and qualitatively through volume fraction measurements for all time points. Histologic analysis was also completed for the Mg and AZ31 screws at 12 weeks, samples were formalin fixed, embedded in plastic, sectioned, and stained with hematoxylin and eosin. For the control samples, after 12 weeks, the mandibles with holes and without screws showed many signs of remodeling. The original holes were not apparent, and new bone growth was seen throughout the region where the holes existed. When compared to naïve control bone, the remodeled bone appeared to be rougher and thicker. After 12 weeks, the stainless steel screws were fully intact. Bone growth occurred around the stainless steel screws, but growth over the screws and bone resorption under the screws were not observed. At 4 weeks, the pure Mg screws were in contact with the bone. Then at 8 weeks the shafts of the pure Mg screws appeared to be mostly degraded, as seen by the presence of holes within the screw bulk in the images, as well as major bone resorption with little new bone formation around the screws. By 12 weeks, the bone resorption seemed to subside, and new bone appeared to be growing over the pure Mg screw in 71% of the screws imaged from both sets of scans, while at the same time bone resorption under the head of the screw was still noted in approximately 85% of the pure Mg screws. The AZ31 screws showed little sign of degradation at 4 weeks, and the surrounding tissue seemed to remain intact. At 8 weeks, the AZ31 screws began to show signs of degradation, with regions of reduced brightness appearing in the shaft region of the screws. The adjacent tissue continued to remodel around the screw, as seen by some new bone growth around the screws, and little bone resorption. At 12 weeks, the AZ31 screws continued to show signs of degradation with a larger area of decreased brightness in the shaft of the screw. The surrounding tissue continued to remodel and grow around the screws. From both sets of scans, there were signs of bone resorption under the head of the screw in approximately 71% of the cases at 12 weeks. Bone grew around and over the head of the AZ31 screws in approximately 57% of the cases for the AZ31 screws at 12 weeks. Histology confirmed the findings noted in the microCT images for pure Mg and AZ31 groups at 12 weeks, identifying the brighter areas around the screws on the images as newly formed bone. The results showed that craniofacial bone remodeling occurred around both Mg-alloy screw types. Pure Mg had a different degradation profile than AZ31, however bone growth occurred around both screw types. The degradation rate of both pure Mg and AZ31 screw types in the bone marrow space and the muscle were faster than in the cortical bone space at 12 weeks.

Several different designs of magnesium bone screws were tested in-vitro and in-vivo to assess the ease of implantation and probability of failure. A set of first generation screws had a design structure which differed from certain embodiments of the invention in that each had a short (or thin) head portion, a flat tip and threading that extended the entire length of the shaft. In comparison, the bone screws according to the invention, a set of third generation screws, had a taller (or thicker) head portion, a pointed tip and threading that did not extend the entire length of the shaft to the head of the screw. The first generation screws were tested in-vitro by drilling holes in excised rabbit mandible bone and inserting the screws in the pre-drilled holes. The results showed that 4 out of 19 failed because the head of the screw was sheared off. Further, it was found that alignment of these screws with the pre-drilled holes was difficult. The third generation screws were also tested in-vitro by drilling holes in excised rabbit mandible bone and inserting the screws in the pre-drilled holes. The results showed that 0 out of 15 failed. The first generation screws, the third generation screws and second generation screws were then tested in-vivo. The second generation screws had a design which included a taller (or thicker) head portion than the first generation screws, a pointed tip and threading that extended the entire length of the shaft. The in-vivo test results showed that the first generation screws failed in 3 out of 4 attempts. The in-vivo failures of the first generation screws occurred due to their inability to be aligned with the pre-drilled holes, i.e., the surgeon was not able to align the screws with the pre-drilled holes in the rabbit mandible. In the in-vivo tests for the second generation screws, problems occurred with the head shearing off the screws in 2 out of 5 attempts. However, with the second generation screws, the pointed tip allowed for ease of alignment in-vivo as compared to the difficulty in aligning the flat tip of the first generation screws. When the third generation screws were implanted, only 5 out of 41 in-vivo attempts failed due to the head being sheared off. Based on the total number of in-vitro and in-vivo tests conducted, the results showed that only 5 out of 56 third generation screws failed compared to 7 out of 23 first generation screws and 2 out of 5 second generation screws.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

We claim:

1. A method of preparing a biodegradable bone screw, comprising:

preparing a magnesium-based alloy;

melting the magnesium-based alloy to form a melted magnesium-based alloy;

introducing the melted magnesium-based alloy into a mold, the mold comprising;

a cylindrical head having a top surface, a bottom planar surface, and a thickness extending between the top surface and bottom planar surface;

a pointed tip;

a cylindrical shaft extending outwardly from the bottom planar surface of the cylindrical head, comprising:

a circumference;

a first end connected to the cylindrical head;

a second end connected to the pointed tip;

a length extending along a linear surface of the shaft between the first and second ends, comprising:

a continuous non-threaded region;

a circumferentially continuous threaded region comprising threads disposed about the circumference of the cylindrical shaft; and a transition point, wherein the continuous non-threaded region extends along an entirety of the length from the first end to the transition point, and the continuous threaded region extends along an entirety of the length from the transition point to the second end; and cooling and solidifying the magnesium-based alloy to have the shape of the mold.

2. A method of employing a biodegradable bone screw to regenerate new tissue in a patient, comprising:

preparing a biodegradable bone screw in accordance with claim 1; and positioning the biodegradable bone screw as a medical implant device.

3. The method of claim 2, wherein the positioning comprises:

forming an opening in tissue of the patient; and implanting the biodegradable bone screw into the opening.

4. The method of claim 2, wherein the medical implant device is selected from the group consisting of a craniofacial bone implant, an orthopedic bone implant and a cardiovascular tissue implant.

5. The method of claim 1, wherein the preparing comprises a process selected from the group consisting of high energy mechanical alloying, uniaxial and isostatic compaction, and sintering.

6. The method of claim 5, wherein the high energy mechanical alloying is conducted under a protective atmosphere.

7. The method of claim 6, wherein the protective atmosphere is effective to preclude, minimize or reduce decomposition of the magnesium-based alloy.

8. The method of claim 6, wherein the protective atmosphere comprises at least one component selected from the group consisting of argon, sulfur hexafluoride and mixtures thereof.

9. The method of claim 5 wherein subsequent to the high energy mechanical alloying, amorphous films are synthesized by pulsed laser deposition.

10. The method of claim 5, further comprising one or more processes selected from the group consisting of casting, forming and finishing.

11. The method of claim 10 wherein the forming is selected from the group consisting of extrusion and forging, and the finishing is selected from the group consisting of mechanical polishing, chemical polishing, and surface treating.

12. The method of claim 1, wherein the magnesium-based alloy, comprises:

from about 0.5 to about 4.0 weight percent yttrium;

from greater than 0 to about 1.0 weight percent calcium;

from about 0.25 to about 1.0 weight percent zirconium; and a remainder of magnesium.

13. The method of claim 1, wherein the magnesium-based alloy, comprises:

from about 1.0 to about 6.0 weight percent zinc;

from greater than 0 to about 1.0 weight percent zirconium; and a remainder of magnesium.

14. The method of claim 12, wherein the magnesium-based alloy further comprises one or more element selected from the group consisting of aluminum, silver, cerium and strontium.

15. The method of claim 13, wherein the magnesium-based alloy further comprises one or more element selected from the group consisting of aluminum, silver, cerium and strontium.

16. A method of remodeling tissue in a patient, comprising:

preparing a magnesium component selected from the group consisting of magnesium and magnesium-based alloy;

melting the magnesium component to form a melted magnesium component;

introducing the melted magnesium component into a mold, the mold comprising;

a cylindrical head having a top surface, a bottom planar surface, a diameter, and a thickness extending between the top surface and bottom planar surface;

a pointed tip;

a cylindrical shaft extending outwardly from the bottom planar surface of the cylindrical head, comprising:

a circumference;

a first end connected to the cylindrical head;

a second end connected to the pointed tip;

a length extending along a linear surface of the shaft between the first and second ends, comprising:

a continuous non-threaded region;

a circumferentially continuous threaded region comprising threads disposed about the circumference of the cylindrical shaft; and a transition point, wherein the continuous non-threaded region extends along an entirety of the length from the first end to the transition point, and the continuous threaded region extends along an entirety of the length from the transition point to the second end; and cooling and solidifying the magnesium-based alloy to have the shape of the mold.

17. The method of claim 16, wherein the thickness is about 1.0 mm and the diameter is from about 1.92 mm to about 2.08 mm or about 2.0 mm.

* * * * *